United States Patent [19]

Kleemann et al.

[11] 4,254,035
[45] Mar. 3, 1981

[54] PROCESS FOR THE PRODUCTION OF 2-ACETAMIDOCINNAMIC ACID

[75] Inventors: Axel Kleemann; Horst Weigel, both of Hanau; Paul Scherberich, Constance, all of Fed. Rep. of Germany

[73] Assignee: Deutsche Gold- und Silber-Scheideanstalt vormals Roessler, Frankfurt, Fed. Rep. of Germany

[21] Appl. No.: 968,923

[22] Filed: Dec. 13, 1978

[30] Foreign Application Priority Data

Dec. 16, 1977 [DE] Fed. Rep. of Germany ....... 2756129

[51] Int. Cl.$^3$ .................. C07D 317/44; C07C 101/42
[52] U.S. Cl. ............................. 260/340.5 R; 560/142; 562/450
[58] Field of Search ..................... 260/340.5 R, 340.5; 562/450

[56] References Cited

U.S. PATENT DOCUMENTS

| 3,347,928 | 10/1967 | Taub et al. ............... 260/340.5 R X |
| 3,878,043 | 4/1975 | Matta et al. ............................. 195/29 |
| 4,124,533 | 11/1978 | Knowles et al. ......... 260/340.5 R X |

OTHER PUBLICATIONS

Org. Synth., Col, vol. 2 (1963), pp. 1–3.
Dakin, J. Biol. Chem., vol. 82 (1929), pp. 439–446.
Bergmann et al., Justus Liebigs Ann. Chem., vol. 448 (1926), pp. 20–31.

*Primary Examiner*—Ethel G. Love
*Attorney, Agent, or Firm*—Cushman, Darby & Cushman

[57] ABSTRACT

2-acetamidocinnamic acid and substituted 2-acetamidocinnamic acids are prepared by reacting glycine with an aromtic aldehyde in the presence of acetic anhydride and a tertiary amine and subsequently treating with water.

26 Claims, No Drawings

PROCESS FOR THE PRODUCTION OF 2-ACETAMIDOCINNAMIC ACID

BACKGROUND OF THE INVENTION

The invention is directed to a process for the production of 2-acetamidocinnamic acid and substituted 2-acetamidocinnamic acids. These compounds are intermediate products in the production of phenyl alanine and its derivatives.

It is known to produce 2-acetamidocinnamic acid by reaction of glycine with benzaldehyde in the presence of acetic anhydride with addition of water free (i.e., anhydrous) sodium acetate and subsequent treatment with water. The yield thereby merely amounts to about 50%. It is also kown to prepare 2-acetamidocinnamic acid in three steps by first reacting glycine with acetic acid to form acetyl glycine, converting this with benzaldehyde under addition of water free sodium acetate into 2-methyl-4-benzylidene-5-oxazolinones and finally converting this with water, in a given case with addition of acetone or sodium hydroxide into the 2-acetamidocinnamic acid. To be sure yields of about 60% are obtained thereby, but the process is expensive. In a similar manner by addition of substituted aromatic aldehydes there are formed the corresponding substituted 2-acetamidocinnamic acids, Dakin, J. Biol. Chem. Vol. 82 (1929), pages 439 to 446; Org. Synth., Col, Vol. 2 (1963) pages 1 to 3.

SUMMARY OF THE INVENTION

There has now been found a process for the production of 2-acetamidocinnamic acid and substituted 2-acetamidocinnamic acids by reacting glycine with an aromatic aldehyde in the presence of acetic anhydride and subsequent treatment with water which is carried out in the presence of a tertiary amine. This process differentiates from the known processes in not requiring the use of sodium acetate. Because of the presence of tertiary amine it is possible to react the glycine with the aldehyde in a simple manner to form 2-acetamidocinnamic acid or a substituted 2-acetamidocinnamic acid and thereby to produce better yields than in the known process.

The process of the invention is particularly suited for the production of 2-acetamidocinnamic acids of the general formula

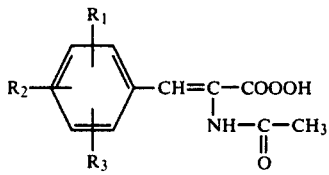

I in which $R_1$, $R_2$ and $R_3$ are the same or different and are straight or branched chain alkyl, alkenyl, cycloalkyl or cycloalkenyl groups, wherein the alkyl groups preferably have 1 to 6, and particularly 1 to 3, carbon atoms, the alkenyl groups preferably have 2 to 6, and particularly 2 to 3, carbon atoms, the cycloalkyl or cycloalkenyl groups preferably have 3 to 8, particularly 3 to 6 carbon atoms in the ring and wherein one or more $CH_2$ can be replaced by O, S or NH, or CH can be replaced by N, aryl groups, aralkyl or alkaryl groups with preferably 1 to 6, and particularly 1 to 3, carbon atoms in the alkyl residue, alkoxy, acyloxy or acylthio groups with preferably 1 to 6, and particularly 1 to 3 carbon atoms, hydrogen, halogen (i.e. fluorine, chlorine or bromine), nitro groups, acylamino groups, hydroxy groups, or amino groups. In a given case $R_1$ can be joined to $R_2$ or $R_2$ with $R_3$ or $R_1$ with $R_3$ to form a saturated or unsaturated ring which ring can also contain one or more oxygen atoms.

To carry out the process glycine is reacted especially with aldehydes of the general formula

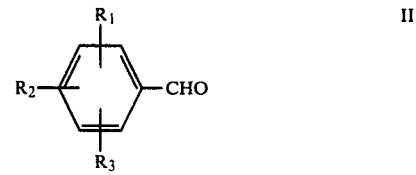

II in which $R_1$, $R_2$ and $R_3$ have the meanings defined above. Suitable aldehydes include for example benzaldehyde, tolylaldehyde (e.g., p-tolylaldehyde, m-tolylaldehyde or o-tolylaldehyde), 4-isopropyl-benzaldehyde, 3,4-methylenedioxy-benzaldehyde, 3,4,5-trimethoxy-benzaldehyde, 4,5-dimethoxy-2-nitro benzaldehyde, 4-phenyl benzaldehyde, 4-chlorobenzaldehyde, 2-bromo-benzaldehyde, 4-fluorobenaldehyde, 4-chloro-3-nitrobenzaldehyde, 4-hydroxybenzaldehyde, vanillin, 4-methoxy-benzaldehyde, salicylaldehyde (2-hydroxy-benzaldehyde),4-acetoxybenzaldehyde, 4-acetylaminobenzaldehyde, 4-dimethylaminobenzaldehyde, 4-nitrobenzaldehyde.

Other suitable aldehydes include 4-ethylbenzaldehyde, 2-hexylbenzaldehyde, 3-butylbenzaldehyde, 4-sec. butylbenzaldehyde, 2-t-butylbenzaldehyde, 4-vinylbenzaldehyde, 2-allylbenzaldehyde, p-hexen-5-ylbenzaldehyde, 4-cyclopropylbenzaldehyde, 4-cyclohexylbenzaldehyde, 2-cyclopentylbenzaldehyde, 4-cyclooctylbenzaldehyde, 4-morpholinobenzaldehyde, 4-tetrahydrofurfurylbenzaldehyde, 4-tetrahydro thienylbenzaldehyde, 4-pyrrolidinylbenzaldehyde, 1-naphthaldehyde, 2-naphthaldehyde, 4-piperidyl benzaldehyde, 4-naphthylbenzaldehyde, 4-p-methylphenyl benzaldehyde, 4-o-methylphenylbenzaldehyde, 4-propylphenylbenzaldehyde, 4-hexylphenylbenzaldenyde, 4-benzalbenzaldehyde, 4-phenethylbenzaldehyde, 4-phenpropylbenzaldehyde, p-hexoxybenzaldehyde, o-propoxybenzaldehyde, p-propoxybenzaldehyde, p-ethoxybenzaldehyde, 4-butoxybenzaldehyde, 2,4-dichlorobenzaldehyde, 3,5-dichlorobenzaldehyde, 3-nitrobenzaldehyde, 4-diethylminobenzaldehyde, 4-dipropylaminobenzaldehyde, 4-propionoxybenzaldehyde, 4-butyroxybenzaldehyde, 4-capronoxybenzaldehyde, 4-acetthiobenzaldehyde, 2,4,6-trichlorobenzaldehyde.

The reaction takes place in the presence of acetic anhydride and tertiary amines. As amines there can be used for example trimethylamine, triethylamine, 1-methylpiperidine, 1-methylpyrrolidine, tri-n-propylamine, benzyl-N, N-dimethylamine, triethanolamine, tributylamine, N-cyclohexyl diethyl amine, 1-methylmorpholine, 1-methylthiomorpholine, N,N-diethanol methylamine and 4-dimethylaminopyridine. Also there can be mentioned N, N-dimethylaniline, trioctylamine, triisopropanolamine, tricetylamine, tris octadecylamine. The preferred amine is triethylamine.

The reaction conditions such as temperature and pressure and the molar ratios of the reactants in a given case are dependent on each other and in a given case depend on the type of reacting materials.

In general the reaction, as well as the subsequent treatment with water, takes place at a temperature of at least 50° C. It is advantageous to use temperatures between about 80° and 200° C., particularly temperatures between 100° C. and the boiling temperature of the mixture. Although the pressure can be chosen as desired, thus the process can be carried out at normal pressure as well as at lower or higher pressure, it is generally advantageous not to deviate substantially from normal pressure. In some cases, however, because of the volatility of the materials at the temperature employed it can be necessary to work at elevated pressure.

The molar ratio of glycine to aldehyde can be selected largely at random, either stoichiometrically or under or over stoichiometrically. Generally it is advantageous to add 1 to 2 moles, especially 1.2 to 1.5 moles of aldehyde per mole of glycine.

It is suitable to add more than one mole of acetic anhydride per mole of glycine. It is advantageous that there be present at least about 2 moles, particularly 3 to 5 moles, of acetic anhydride per mole of glycine.

There is suitably used at least about 0.3 mole, preferably 0.5 to 2.0 moles, particularly 0.8 to 1.2 moles, of tertiary amine per mole of glycine.

In some cases it can be advantageous in the treatment with water to have present an organic solvent for example acetone.

Unless otherwise indicated all parts and percentages are by weight. The process can comprise, consist essentially of or consist of the steps set forth and the materials can comprise, consist essentially of or consist of those set forth.

DESCRIPTION OF THE PREFERRED EMBODIMENTS

EXAMPLE 1

A mixture of 75 grams (1.0 mole) of glycine, 388 grams (3.8 moles) of acetic anhydride, 149 grams (1.4 moles) of benzaldehyde and 101 grams (1.0 mole) of triethylamine were heated and first held for 2 hours at the reflux temperature and then after addition of 1800 ml of water held at reflux for a further 1.5 hours. The mixture was then immediately treated with activated carbon and clarified. In the cooling to room temperature the 2-acetamidocinnamic acid separated out. The yield amounted to 133 grams, corresponding to 65% based on the glycine added. The 2-acetamidocinnamic acid has a melting point of 188° to 190° C. It was homogeneous, as was established by thin layer chromatography.

EXAMPLE 2

The procedure was the same as in Example 1 but there were employed 59 grams (1.0 mole) of trimethylamine in place of triethylamine. The yield of 2-acetamidocinnamic acid was 140 grams, corresponding to 68%.

EXAMPLE 3

The procedure was the same as in Example 1 but there were added 74 grams (0.75 mole) of 1-methyl-piperidine in place of triethylamine. The yield of 2-acetamidocinnamic acid was 125 grams, corresponding to 61%.

EXAMPLE 4

A mixture of 75 grams (1.0 mole) of glycine, 408 grams (4.0 moles) of acetic anhydride, 146 grams (1.2 moles) of salicylaldehyde and 101 grams (1.0 mole) of triethylamine were heated and first held for 2.5 hours at the reflux temperature and then after addition of 1500 ml of water held at reflux for a further 2.0 hours. In the cooling of the reaction mixture to room temperature 180 grams of o-acetoxy-2-acetamidocinnamic acid separated out. This corresponds to a yield of 66% based on the glycine added. The o-acetoxy-2-acetamidocinnamic acid has a melting point of 202° to 203° C.

EXAMPLE 5

A mixture of 75 grams (1.0 mole) of glycine, 196 grams (1.3 moles) of 4-nitro-benzaldehyde, 357 grams (3.5 moles) of acetic anhydride and 115 grams (0.8 mole) of tri-n-propylamine were heated and first held for 3 hours at the reflux temperature and then after addition of 2000 ml of water held at reflux for a further 1.5 hours. There were recovered 170 grams of 2-acetamido-p-nitrocinnamic acid. corresponding to a yield of 68% based on the glycine added. The 2-acetamido-p-nitrocinnamic acid had a melting point of 233 to 234%.

EXAMPLE 6

A mixture of 225 grams (1.5 moles) of 3,4-methylenedioxybenzaldehyde, 75 grams (1.0 mole) of glycine, 357 grams (3.5 moles) of acetic anhydride and 135 grams (1.0 mole) of N, N-dimethylbenzylamine were heated and first held for 3 hours at the reflux temperature and then after the addition of 1800 ml of water held at reflux for a further 1.5 hours. There were recovered 162 grams of 2-acetamido-3,4-methylenedioxycinnamic acid, corresponding to a yield of 65% based on the glycine added. The material had a melting point of 220° to 221° C.

What is claimed is:

1. In a process for the production of 2-acetamidocinnamic or a ring substituted 2-acetamidocinnamic acid by reacting glycine with an aromatic aldehyde in the presence of acetic anhydride and subsequently treating with water the improvement comprising carrying out the process in the presence of a tertiary amine at at least 50° C.

2. The process of claim 1 wherein the 2-acetamidocinnamic acid or substituted cinnamic acid has the formula

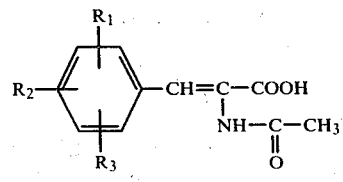

and the starting aldehyde has the formula

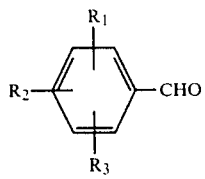

where $R_1$, $R_2$ and $R_3$ are hydrogen, alkyl, alkenyl, cycloalkyl, cycloalkenyl, cycloalkyl having at least one $CH_2$ group replaced by O, S or NH, cycloalkenyl having a CH replaced by N, aryl, aralkyl, alkaryl, alkoxy, acyloxy, acylthio, halogen, nitro, acylamino, hydroxy or amino or $R_1$ together with $R_2$, $R_1$ together with $R_3$ or $R_2$ together with $R_3$ are joined to form a saturated ring with 0 to 2 oxygen atoms or are joined to form an unsaturated ring.

3. The process of claim 2 wherein $R_1$, $R_2$ and $R_3$ are hydrogen, alkyl of 1 to 6 carbon atoms, alkenyl of 2 to 6 carbon atoms, cycloalkyl of 3 to 8 carbon atoms in the cycloalkyl group, cycloalkenyl of 3 to 8 carbon atoms in the cycloalkenyl group, phenyl, naphthyl, aralkyl with 1 to 6 carbon atoms in the alkyl group, alkaryl with 1 to 6 carbon atoms in the alkyl group, alkoxy with 1 to 6 carbon atoms, acyloxy with 1 to 6 carbon atoms in the acyl, acylthio with 1 to 6 carbon atoms in the acyl, halogen of atomic weight 9 to 80, nitro, hydroxy, acylamino with 1 to 6 carbon atoms in the acyl group, dialkylamino with 1 to 6 carbon atoms in the alkyl group or two members of $R_1$, $R_2$ and $R_3$ together from a methylenedioxy group.

4. The process of claim 3 wherein $R_1$, $R_2$ and $R_3$ are hydrogen alkyl of 1 to 3 carbon atoms, alkenyl of 2 to 3 carbon atoms, cycloalkyl of 3 to 6 carbon atoms in the cycloalkyl group, cycloalkenyl of 3 to 6 carbon atoms in the cycloalkenyl group, phenyl, phenalkyl having 1 to 3 carbon atoms in the alkyl residue, alkylphenyl having 1 to 3 carbon atoms in the alkyl residue, alkoxy having 1 to 3 carbon atoms, alkanoyloxy having 1 to 3 carbon atoms, alkanoylthio having 1 to 3 carbon atoms, halogen of atomic weight 9 to 80, nitro, hydroxy, alkanoylamino having 1 to 3 carbon atoms, dialkyl amino having 1 to 3 carbon atoms in each alkyl group or $R_1$ and $R_2$ together are methylenedioxy and $R_3$ is hydrogen.

5. The process of claim 4 wherein $R_1$, $R_2$ and $R_3$ are hydrogen, alkyl of 1 to 3 carbon atoms, alkoxy of 1 to 3 carbon atoms, phenyl, halogen of atomic weight 9 to 80, nitro, hydroxy, dialkylamino having 1 to 3 carbon atoms in each alkyl group, alkanoyloxy having 1 to 3 carbon atoms, alkanoylamino having 1 to 3 carbon atoms or $R_1$ and $R_2$ together are methylenedioxy.

6. The process of claim 5 wherein the aldehyde is benzaldehyde, tolylaldehyde, 4-isopropylbenzaldehyde, 3,4-methylenedioxybenzaldehyde, 3,4,5-trimethoxybenzaldehyde, 2-nitro-4,5-dimethoxybenzaldehyde, 4-phenylbenzaldehyde, 4-chlorobenzaldehyde, 2-bromobenzaldehyde, 4-fluorobenzaldehyde, 3-nitro-4-chlorobenzaldehyde, 4-hydroxybenzaldehyde, salicylaldehyde, vanillin, 4-methoxybenzaldehyde, 4-dimethylaminobenzaldehyde, 4-nitrobenzaldehyde, 4-acetoxybenzaldehyde, or 4-acetylaminobenzaldenyde.

7. The process of claim 6 wherein the aldehyde is benzaldehyde.

8. The process of claim 6 wherein the aldehyde is salicylaldehyde.

9. The process of claim 6 wherein the aldehyde is 4-nitrobenzaldehyde.

10. The process of claim 6 wherein the aldehyde is 3,4-methylenedioxybenzaldehyde.

11. The process of claim 3 wherein there is employed 0.5 to 2.0 moles of tertiary amine per mole of glycine.

12. The process of claim 11 wherein the temperature is between 100° C. and the boiling temperature of the reaction mixture.

13. The process of claim 12 wherein the aldehyde is employed in an amount of 1 to 2 moles per mole of glycine.

14. The process of claim 13 wherein there is employed 2 to 5 moles of acetic anhydride per mole of glycine.

15. The process of claim 14 wherein there are employed 1.2 to 1.5 moles of aldehyde per mole of glycine, 3 to 5 moles of acetic anhydride per mole of glycine and 0.8 to 1.2 moles of tertiary amine per mole of glycine.

16. The process of claim 3 wherein the temperature is between 100° C. and the boiling temperature of the reaction mixture.

17. The process of claim 3 wherein there is employed at least 0.3 mole of tertiary amino per mole of glycine.

18. The process of claim 1 wherein there are employed 0.5 to 2.0 moles of tertiary amine per mole of glycine.

19. The process of claim 1 wherein the temperature is 50° to 200° C.

20. The process of claim 19 wherein the temperature is 80° to 200° C.

21. The process of claim 1 wherein the tertiary amine is a trialkylamine having 1 to 18 carbon atoms in the alkyl groups.

22. The process of claim 21 wherein the amine is trimethylamine, triethylamine or tripropylamine.

23. The process of claim 22 wherein the amine is triethylamine.

24. The process of claim 23 wherein the aldehyde is benzaldehyde or salicylaldehyde.

25. The process of claim 22 wherein the aldehyde is benzaldehyde, salicylaldehyde or 4-nitro benzaldehyde.

26. The process of claim 1 consisting essentially of reacting glycine with an aromatic aldehyde in the presence of acetic anhydride and a tertiary amine and subsequently treating with water.

* * * * *